US010499959B2

(12) United States Patent
Heuer et al.

(10) Patent No.: US 10,499,959 B2
(45) Date of Patent: Dec. 10, 2019

(54) HANDLING INSTRUMENT FOR A BONE ANCHOR

(71) Applicant: SILONY MEDICAL INTERNATIONAL AG, Frauenfeld (CH)

(72) Inventors: Frank Heuer, Filderstadt (DE); Ralf Riesinger, Tuttlingen-Nendingen (DE); Timo Ohnmacht, Trichtingen (DE)

(73) Assignee: SILONY MEDICAL INTERNATIONAL AG, Frauenfeld (CH)

( * ) Notice: Subject to any disclaimer, the term of this patent is extended or adjusted under 35 U.S.C. 154(b) by 159 days.

(21) Appl. No.: 15/750,315

(22) PCT Filed: Aug. 3, 2016

(86) PCT No.: PCT/EP2016/068582

§ 371 (c)(1),
(2) Date: Feb. 5, 2018

(87) PCT Pub. No.: WO2017/021469

PCT Pub. Date: Feb. 9, 2017

(65) Prior Publication Data

US 2018/0221060 A1 Aug. 9, 2018

(30) Foreign Application Priority Data

Aug. 4, 2015 (DE) ........................ 10 2015 214 874

(51) Int. Cl.
*A61B 17/70* (2006.01)

(52) U.S. Cl.
CPC .................................. *A61B 17/708* (2013.01)

(58) Field of Classification Search
CPC .............................. A61B 17/70; A61B 17/708
See application file for complete search history.

(56) References Cited

U.S. PATENT DOCUMENTS 8,439,922 B1 5/2013 Arnold et al.
2008/0319477 A1 12/2008 Justis et al.
(Continued)

FOREIGN PATENT DOCUMENTS

AT 20608 B 10/1905
DE 202004021979 U1 10/2014
EP 2692304 A1 2/2014

OTHER PUBLICATIONS

International Search Report and Written Opinion Form PCT/ISA/210 and PCT/ISA/237, International Application No. PCT/EP2016/068582, pp. 1-11, International Filing Date Aug. 3, 2016, dated Dec. 5, 2016.

*Primary Examiner* — Christopher J Beccia
(74) *Attorney, Agent, or Firm* — Bond Schoeneck & King, PLLC; George McGuire

(57) ABSTRACT

The invention relates to a handling instrument for connecting to a bone anchor, comprising a first outer and a second inner sleeve-shaped housing part with a respective longitudinal direction, a first housing part internal thread which extends in the respective longitudinal direction, and a second housing part external thread. The handling instrument is characterized by a threadless section of the first housing part in the region of the internal thread, said section extending distally from a proximal longitudinal end of the internal thread in the longitudinal direction and in a circumferential direction, and the handling instrument is characterized in that the outer thread of the second housing part is formed only in the region of the extension of the threadless section such that the second housing part can be plugged into the first housing part in the longitudinal direction in a translational manner at a suitable rotational position and can subsequently be screwed into the internal thread of the first housing part.

14 Claims, 6 Drawing Sheets

4 30 2 8 23 10 12 44 28 26 40 38 49 32 43 46 22 18 43 50 36 6 20 24 42 52 34 54 48

(56) References Cited

U.S. PATENT DOCUMENTS

| | | | |
|---|---|---|---|
| 2012/0253413 | A1 | 10/2012 | Runco et al. |
| 2013/0204263 | A1 | 8/2013 | Jones et al. |

HANDLING INSTRUMENT FOR A BONE ANCHOR

CROSS-REFERENCE TO RELATED APPLICATIONS

This application is the United States National Phase Entry of PCT Application No. PCT/EP2016/068582, filed Aug. 3, 2016, which claims priority to German Application No. 10-2015-214874.2 (DE), filed Aug. 4, 2015, the entire disclosure of each of which is incorporated herein by reference.

BACKGROUND OF THE INVENTION

The invention relates to a handling instrument for a bone anchor, in particular a bone screw, in particular a pedicle screw in spinal surgery, the instrument being detachably, but also rigidly and non-rotatably, connectable to a head of the bone anchor and extending in an axial longitudinal direction, said instrument comprising a first outer housing part extending in the longitudinal direction and a second inner housing part which extends in the longitudinal direction and can be inserted into the first outer housing part in the longitudinal direction, the housing parts being tubular or sleeve-shaped, at least in sections, and the first outer housing part including an internal thread which extends in the longitudinal direction, and the second inner housing part including an external thread which extends in the longitudinal direction and can be screwed into the internal thread, the first outer housing part engaging behind the head of the bone anchor in the longitudinal direction, and the second inner housing part, when screwed in, being capable of being supported against the head of the bone anchor in the longitudinal direction such that the instrument can thus be detachably fastened to the head of the bone anchor.

Handling instruments of this kind are known.

Accordingly, the problem addressed by the present invention is that of improving the handling instrument such that it is easier for surgeons to use.

SUMMARY OF THE INVENTION

According to the invention, this problem is solved by a handling instrument of the stated kind by the first outer housing part including a threadless section in the region of the internal thread, which section extends distally from a proximal longitudinal end of the internal thread in the longitudinal direction and over an angular segment in the circumferential direction, and by the external thread of the second inner housing part being formed, from a distal longitudinal end of the external thread, only in the region of the extension of the threadless section of the first outer housing part such that the second inner housing part can be plugged into the first outer housing part in the longitudinal direction in a translational manner at a suitable rotational position until the distal longitudinal end of the external thread comes into contact with a distal end of the threadless section, i.e. with the internal thread, and can subsequently be screwed into the internal thread of the first outer housing part. Owing to the design of the handling instrument according to the invention, the second inner housing part does not have to be screwed over the entire travel range thereof when joining with the first outer housing part, rather—as explained above—the inner housing part can be plugged into the outer housing part in a translational manner at the beginning of the joining process. According to the invention, this is made possible by the external thread of the inner housing part not being formed continuously in the circumferential direction according to the invention, but being formed only in the region mentioned, which extends in the longitudinal direction and is located within the extension of the threadless section of the outer housing part. This is what makes the translational plug-in movement possible at the beginning of the joining process. The inner housing part can thus be joined or plugged in, over the longitudinal extension of the threadless section, in the longitudinal direction in a translational manner at a suitable rotational position until the distal longitudinal end of the external thread section comes into contact, at the distal end of threadless section, with the internal thread of the outer housing part, which internal thread preferably extends in the full circumferential direction. At this point, the inner housing part is screwed into the outer housing part by a rotational screwing movement.

In order to form the threadless section in the first outer housing part, for example initially an internal thread which is continuous in the circumferential direction could be formed, which is later removed, in regions, for example by machining. In contrast, it may prove to be advantageous for the threadless section of the first outer housing part to be designed such that the first outer housing part includes a recess in the wall thereof, which recess is radial with respect to the longitudinal direction and continuous towards the outside. The recess can be produced for example when the outer housing part is still in the flat-material state, for instance by a simple punching action. A further significant advantage is that the user immediately identifies where the threadless section is formed in the first outer housing part on account of the continuous, window-like recess. This allows simple and intuitive positioning of the second inner housing part in the rotational position.

With respect to the dimensions of the threadless section of the first outer housing part, it is advantageous for the threadless section to include an extension of from 3 to 20 mm in the circumferential direction, and 5 to 100 mm in the longitudinal direction.

It is also advantageous, in terms of achieving a stable connection between the housing parts, for the first outer housing part to include two threadless sections which are opposite one another in a manner that is diametrical to the longitudinal direction. This makes it possible for the inner housing part to also have an external thread section on each of the diametrically opposed sides. This results in the forces which occur when the two parts are screwed together being more evenly distributed and absorbed.

The first outer housing part could for example have a rigid, substantially cylindrical shape and, by means of recesses and projections, could be brought into a position in which it engages behind the head of the bone anchor. In contrast, it is advantageous for the first outer housing part to include two mutually diametrical, half-shell-shaped legs which can be deflected against one another, in a manner that is slightly transverse to the longitudinal direction, such that they can reach a rear-engagement position at the head of the bone anchor, in particular by latching or snapping, and thus receive a proximal end of the head of the bone anchor therebetween. In this manner, resilient deflectability of the half-shell-shaped legs allows a restoring force to be produced for receipt, with zero clearance, at the head of the bone anchor.

It is also advantageous for the second inner housing part to include a first distal section, and a proximal section including the external thread, which sections can be rotated relative to one another about the axial longitudinal direction by means of a rotational joint. In this manner, when the second inner housing part and the first outer housing part are screwed together, only the proximal section of the inner housing part is rotated in the circumferential direction; the distal section is decoupled from the rotational movement by the rotational joint and is inserted in a translational manner.

According to an advantageous embodiment of the invention, longitudinal guide means are provided for guided receipt of the second inner housing part in the first outer housing part. The first distal section of the second inner housing part is guided by said means so as to be able to be received in the first outer housing part such that said section cannot rotate relative to said first outer housing part.

It would also be conceivable for the longitudinal guide means to allow receipt of the second inner housing part in the first outer housing part only in a discrete rotational position.

According to a further embodiment of the invention, the first outer housing part includes an additional distal longitudinal guide means in a distal end region. Said means may be formed for example by at least one radially inwardly protruding projection, which is in particular mushroom-shaped or T-shaped, in the distal end region of the outer housing part. The second inner housing part includes a recess which engages with the projection and which, advantageously from a distal end of the second inner housing part, is open-edged and extends in the longitudinal direction. When the second inner housing part and the first outer housing part are screwed together, the distal section of the second inner housing part, which is decoupled from the rotational movement by the rotational joint, is guided by said longitudinal guide means in the longitudinal direction.

According to a further embodiment of the invention, the first outer housing part includes an in particular radial recess through which the position of the second inner housing part, relative to the first outer housing part in the longitudinal direction, is visually perceptible. This can be made possible by the second inner housing part having a visually perceptible marking on the outside. This allows the desired correct positioning of the second inner housing part relative to the first outer housing part in the longitudinal direction.

According to a further embodiment of the invention, the second inner housing part includes, at a proximal end, one or more tool application points in order to make it easier to screw the second inner housing part into the first outer housing part. A suitable tool may be applied at said tool application points such that the second inner housing part can be rotated thereby about the longitudinal direction.

BRIEF DESCRIPTION OF THE DRAWINGS

Preferred developments are described in the dependent claims, for which protection is claimed in any desired combination, and a preferred embodiment of the handling instrument according to the invention is set out in the drawings and subsequent description, in which drawings:

DETAILED DESCRIPTION

Figure 1:
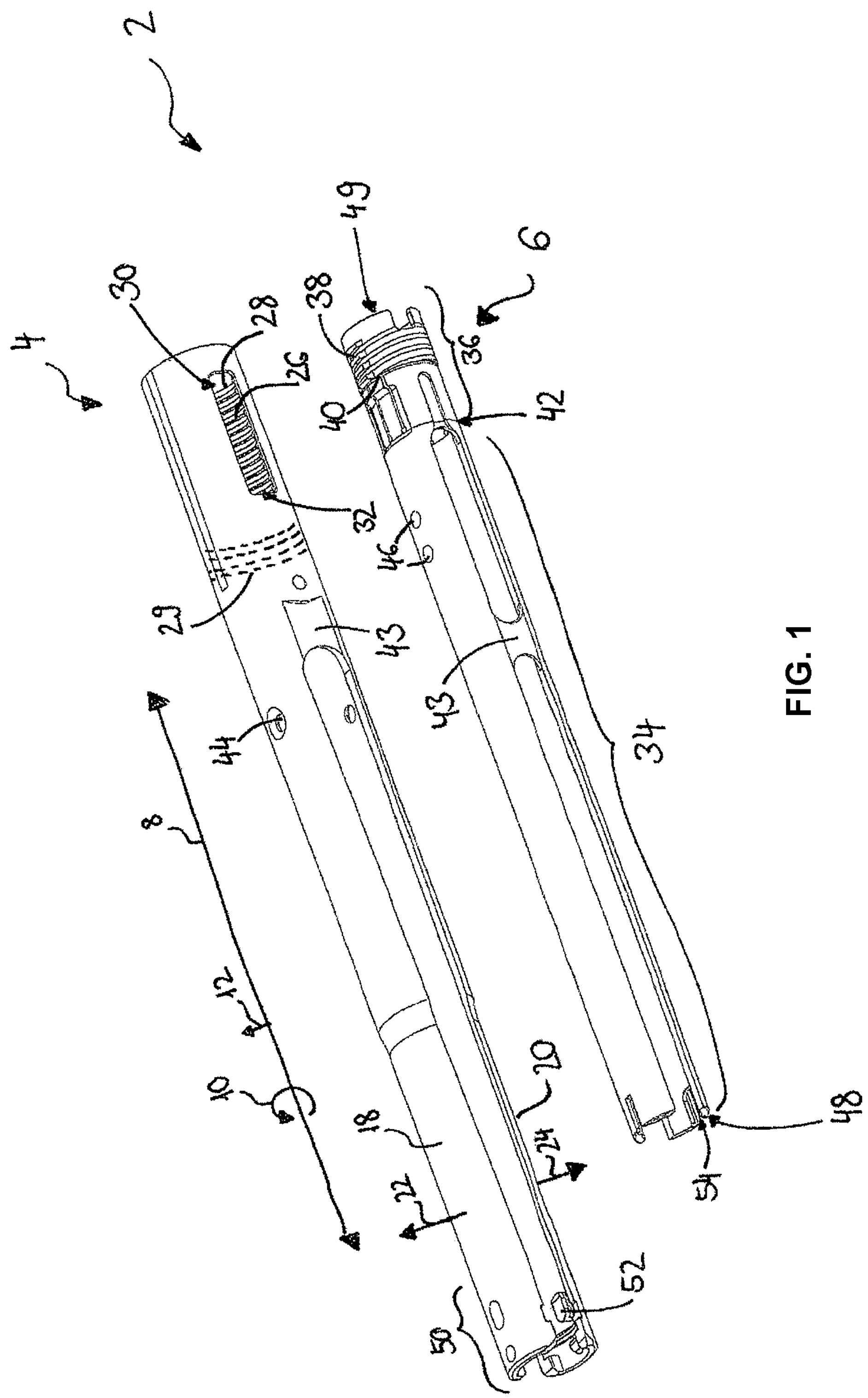
FIGS. 1, 2 and 3 are each views of the handling instrument according to the invention.

The drawings show a handling instrument according to the invention, which is denoted as a whole by reference sign

2. Said instrument comprises a first outer housing part 4 and a second inner housing part 6, as well an axial longitudinal direction 8, a circumferential direction 10 and a radial direction 12. The two housing parts shown by way of example are roughly tubular or sleeve-shaped, and designed such that the second inner housing part 6 can be inserted into the first outer housing part 4 in the longitudinal direction 8.

The handling instrument 2 according to the invention can be detachably fastened to a bone anchor 14, the first outer housing part 4 engaging behind a head 16 of the bone anchor 14 in the longitudinal direction 8, and the second inner housing part 6 being capable of being supported against the head 16 of the bone anchor in the longitudinal direction 8. For this purpose, the first outer housing part 4 includes two mutually diametrical, half-shell-shaped legs 18, 20 which can be deflected, in a manner that is slightly transverse to the longitudinal direction 8, i.e. in the direction of the arrows 22, 24, such that they reach a rear-engagement position at the head 16 of the bone anchor.

In order for the second inner housing part 6 to be able to be plugged into the first outer housing part 4 in a translational manner and subsequently screwed in, the first outer housing part 4 comprises an internal thread 26 having a proximal end 28 and a distal end 29, which is indicated in FIG. 1 but cannot be seen. Furthermore, a window-like recess can be seen in the region of the internal thread 26, which recess forms a threadless section 30 having a distal end 32. The threadless section 30 extends in the longitudinal direction from the proximal end 28 of the internal thread 26. A recess of this kind is likewise provided in the side of the first outer housing part 4 that is opposite in the radial direction 12.

The second inner housing part 6 comprises a distal section 34, a proximal section 36 having an external thread 38 and a rotational joint 42 between the distal section 34 and the proximal section 36. As can be seen in FIG. 1, the external thread 38, which comprises a distal longitudinal end 40, does not extend over the entire circumference of the second inner housing part 6 in the circumferential direction 10, rather, said thread is provided only in a region that complements the threadless section 30 of the first outer housing part 4. The external thread 38 extends only over a circumferential angular segment that is slightly smaller than the circumferential angular segment over which the threadless section 30 extends. A thread of this kind is likewise provided on the side of the second inner housing part 6 that is opposite in the radial direction 12.

The second inner housing part 6 can be plugged into the first outer housing part 4 in the longitudinal direction 8 in a translational manner at a suitable rotational position. For guided receipt of the second inner housing part 6 in the first outer housing part 4, the housing parts 4, 6 have longitudinal guide means 43 in the form of mutually complementary wall regions. The second inner housing part 6 can thus be plugged into the first outer housing part 4 in a translational manner when the longitudinal guide means 43 of the two housing parts 4, 6 are in a suitably aligned position with respect to one another, and the external thread 38 of the second inner housing part 6 is aligned with the threadless section 30 of the second outer housing part 4.

The second inner housing part 6 can be plugged into the first outer housing part 4 in a translational manner until the distal longitudinal end 40 of the external thread 38 comes into contact with the distal end 32 of the threadless section 30. The external thread 38 can then be screwed into the internal thread 26 of the first outer housing part 4. In the process, only the proximal section 36 of the second inner housing part 6 is rotated in the circumferential direction 10 about the axial longitudinal direction 8; the distal section 34 of the second inner housing part 6 is decoupled from the rotational movement by the rotational joint 42 and, guided by the longitudinal guide means 43, is inserted in the longitudinal direction 8.

Figure 2:
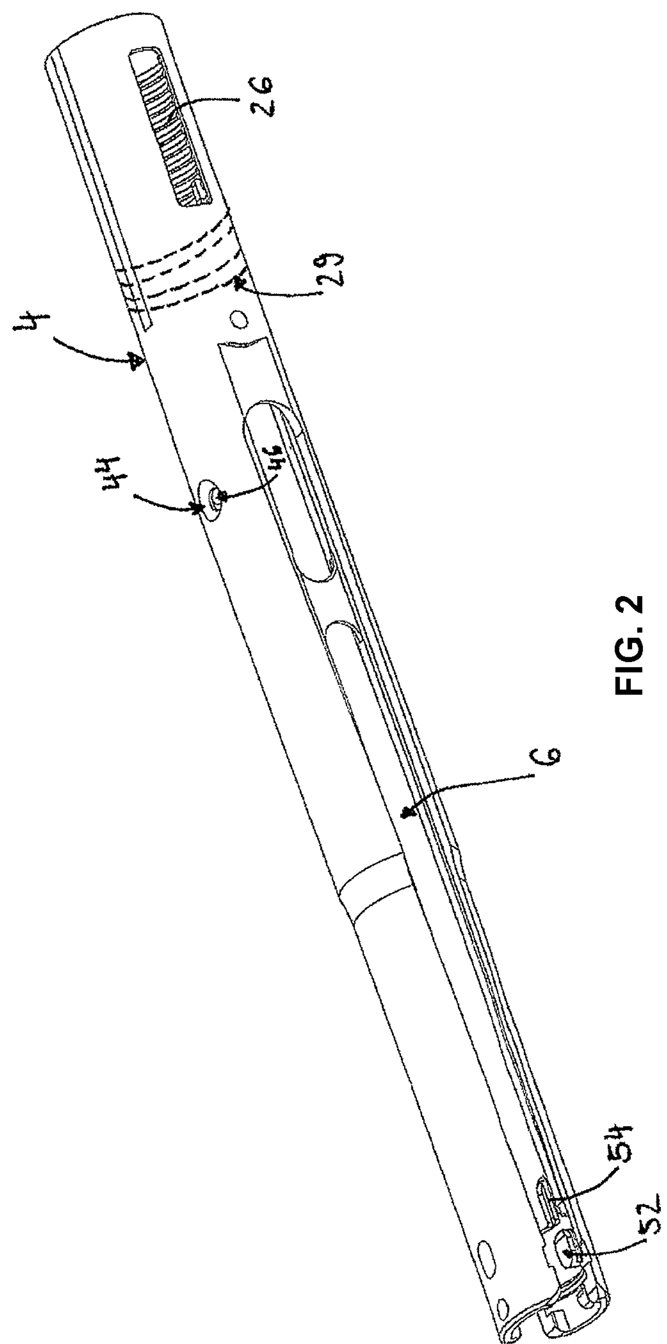
Figure 3:
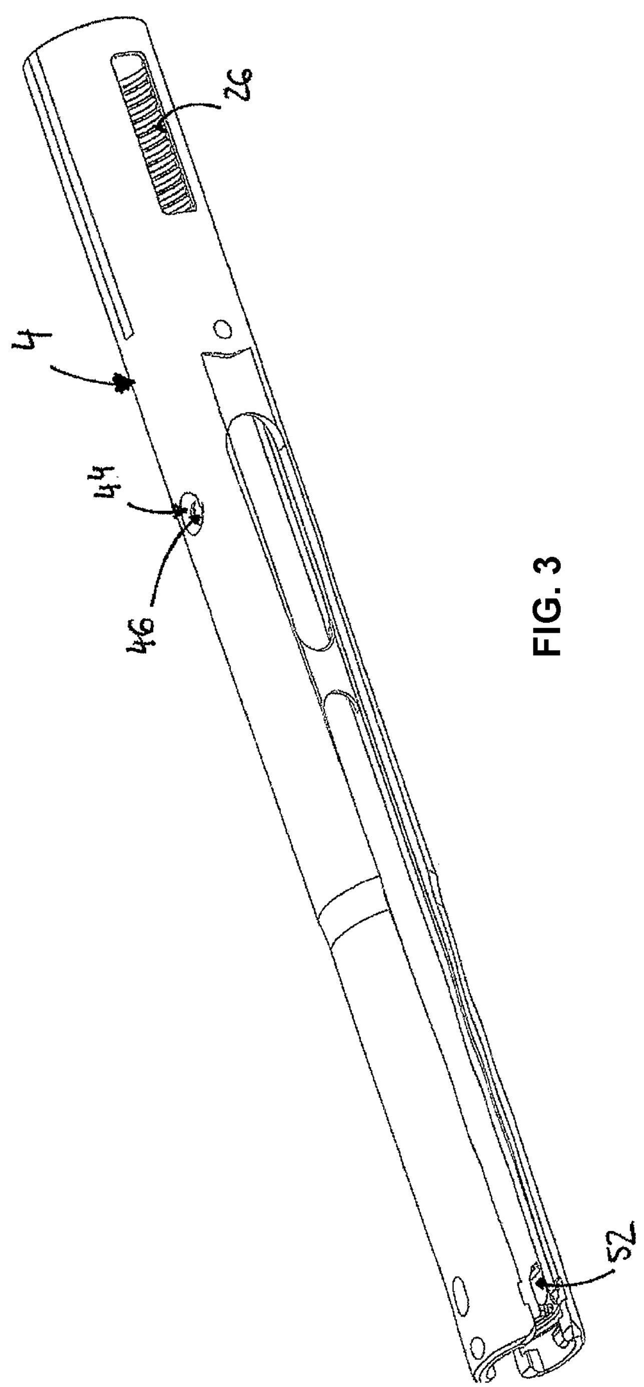

FIGS. 2 and 3 show the first outer housing part 4 having the second inner housing part 6 inserted therein. The first outer housing part 4 includes a radial recess 44 through which a visually perceptible marking 46 can be seen, which marking is applied to the second inner housing part 6.

Figure 4:
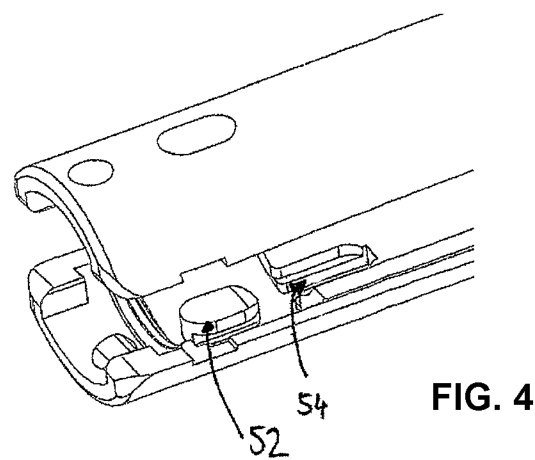
FIG. 4. shows a detail from FIG. 2.
Figure 5:
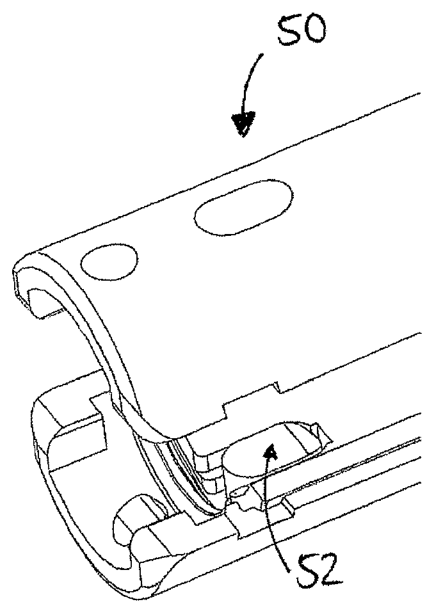
FIG. 5 shows a detail from FIG. 3.

FIGS. 4 and 5 show, as a detail from FIGS. 2 and 3, a distal end 48 of the second inner housing part 6 in a distal end region 50 of the first outer housing part 4. A radially inwardly protruding projection 52 on the first outer housing part 4 is for example T-shaped when viewed in the longitudinal direction 8. In FIG. 5, the radially inwardly protruding projection 52 on the first outer housing part 4 is received by a recess 54 in the second inner housing part 6, which recess complements the projection 52. The projection 52 and the recess 54 form a dovetail guide for form-fittingly guiding the housing parts 4, 6. The second inner housing part 6 can be inserted into the first outer housing part 4 and screwed in until the end face of said inner housing part is supported on the head of the bone anchor 16.

Figure 6:
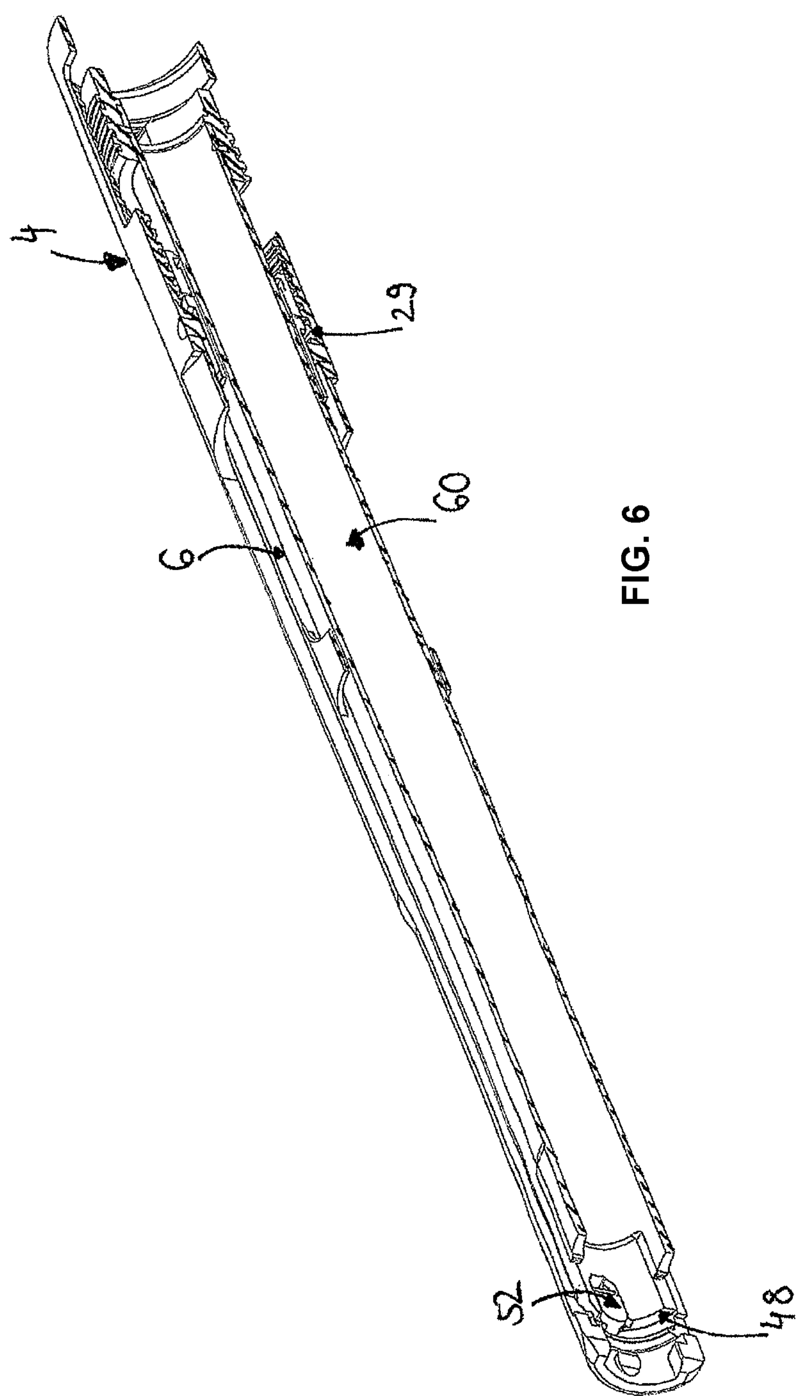
FIG. 6 is a longitudinal sectional view of the handling instrument according to the invention from FIG. 1 and a rod pressure part from FIG. 7 located therein.
Figure 7:
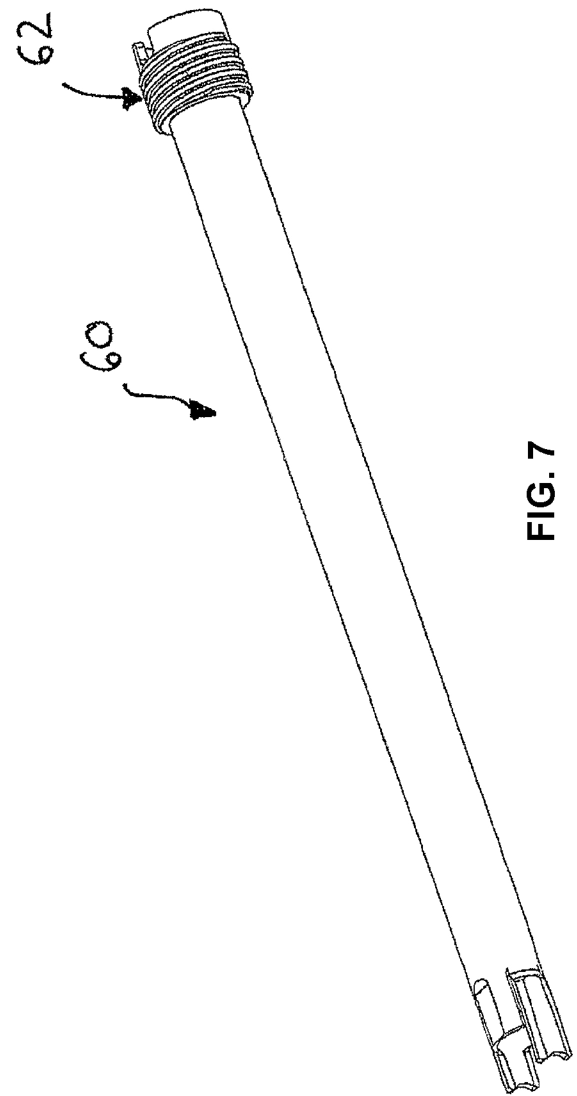
FIG. 7 shows the rod pressure part.

FIG. 7 shows a rod pressure part, which is denoted as a whole by reference sign 60. In order for the rod pressure part 60 to be able to be screwed into the internal thread 26 of the first outer housing part 4, the rod pressure part 60 comprises an external thread 62. Said part can then exert an actuating force on a correction rod that is inserted in the bone anchor. FIG. 6 is a longitudinal sectional view of the handling instrument 2 having the rod pressure part 60 located therein.

What is claimed is:

1. Handling instrument for a bone anchor, in particular a bone screw, in particular a pedicle screw in spinal surgery, the instrument being detachably, but also rigidly and non-rotatably, connectable to a head of the bone anchor and extending in an axial longitudinal direction, said instrument comprising a first outer housing part extending in the longitudinal direction and a second inner housing part which extends in the longitudinal direction and can be inserted into the first outer housing part in the longitudinal direction, the housing parts being tubular or sleeve-shaped, at least in sections, and the first outer housing part including an internal thread which extends in the longitudinal direction, and the second inner housing part including an external thread which extends in the longitudinal direction and can be screwed into the internal thread, the first outer housing part engaging behind the head of the bone anchor in the longitudinal direction, and the second inner housing part, when screwed in, being supported against the head of the bone anchor in the longitudinal direction such that the instrument can thus be detachably fastened to the head of the bone anchor, characterized in that the first outer housing part includes a threadless section in the region of the internal thread, which section extends distally from a proximal longitudinal end of the internal thread in the longitudinal direction and over an angular segment in a circumferential direction, and in that the external thread of the second inner housing part is formed, from a distal longitudinal end of the external thread, only in the region of the extension of the threadless section of the first outer housing part such that the second inner housing part can be plugged into the first outer housing part in the longitudinal direction in a translational manner at a suitable rotational position until the distal longitudinal end of the external thread comes into contact with a distal end of the threadless section, and can subsequently be screwed into the internal thread of the first outer housing part.

2. Handling instrument according to claim 1, characterized in that the threadless section of the first outer housing part is formed by the first outer housing part including a recess in the wall thereof, which recess is radial with respect to the longitudinal direction and continuous towards the outside.

3. Handling instrument according to claim 1, characterized in that the threadless section of the first outer housing part includes an extension of from 3 to 20 mm in the circumferential direction, and 5 to 100 mm in the longitudinal direction.

4. Handling instrument according to claim 1, characterized in that the first outer housing part includes two threadless sections which are opposite one another in a manner that is diametrical to the longitudinal direction.

5. Handling instrument according to claim 4, characterized in that the external thread of the second inner housing part is formed, from a distal longitudinal end of the external thread, only in the region of the two threadless sections.

6. Handling instrument according to claim 1, characterized in that the first outer housing part includes two mutually diametrical, half-shell-shaped legs which can be deflected, in manner that is slightly transverse to the longitudinal direction, such that they reach a rear-engagement position at the head of the bone anchor, in particular by latching or snapping, and thus receive a proximal end of the head of the bone anchor therebetween.

7. Handling instrument according to claim 1, characterized in that the second inner housing part includes a first distal section, and a proximal section including the external thread, which sections can be rotated relative to one another about the axial longitudinal direction by means of a rotational joint.

8. Handling instrument according to claim 7, characterized in that the first distal section of the second inner housing part is guided by longitudinal guide means so as to be able to be received in the first outer housing part such that said section cannot rotate relative to said first outer housing part.

9. Handling instrument according to claim 8, characterized in that the longitudinal guide means allow the second inner housing part to be received in the first outer housing part only in a discrete rotational position.

10. Handling instrument according to claim 1, characterized in that at least one radially inwardly protruding projection is formed in a distal end region of the first outer housing part, which projection forms a distal longitudinal guide means for the second inner housing part, the second inner housing part including a recess which engages with the projection.

11. Handling instrument according to claim 10, characterized in that the projection is mushroom-shaped or T-shaped when viewed in the longitudinal direction or in section.

12. Handling instrument according to claim 10, characterized in that the recess in the second inner housing part, from a distal end of the second inner housing part, is open-edged and extends in the longitudinal direction.

13. Handling instrument according to claim 1, characterized in that at least one radial recess is formed in the first outer housing part, through which recess a marking on the outside of the second inner housing part is visually perceptible when the second inner housing part is in a specific position relative to the first outer housing part in the longitudinal direction.

14. Handling instrument according to one or more of the preceding claims, characterized in that the inner housing part includes, at the proximal end, one or more tool application points, and a suitable tool can be applied such that the second inner housing part can be rotated thereby in a rotational movement about the axis.

* * * * *